(12) United States Patent
Kotera et al.

(10) Patent No.: US 8,876,361 B2
(45) Date of Patent: Nov. 4, 2014

(54) FLUID AGITATION METHOD, FLUID AGITATION SYSTEM, AND CARTRIDGE

(75) Inventors: Hidetoshi Kotera, Kyoto (JP); Takaaki Suzuki, Takamatsu (JP); Kensuke Kanda, Himeji (JP); Yuichiro Noda, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 1079 days.

(21) Appl. No.: 12/934,030

(22) PCT Filed: Mar. 27, 2009

(86) PCT No.: PCT/JP2009/056932
§ 371 (c)(1),
(2), (4) Date: Sep. 22, 2010

(87) PCT Pub. No.: WO2009/119918
PCT Pub. Date: Oct. 1, 2009

(65) Prior Publication Data
US 2011/0019497 A1   Jan. 27, 2011

(30) Foreign Application Priority Data

Mar. 28, 2008  (JP) .................. 2008-085779

(51) Int. Cl.
*B01F 11/00* (2006.01)
*B01F 11/02* (2006.01)
*G01N 33/49* (2006.01)

(52) U.S. Cl.
CPC ............ *B01F 11/0266* (2013.01); *G01N 33/49* (2013.01)
USPC ........................................................ 366/127

(58) Field of Classification Search
CPC .. B01F 11/02; B01F 11/0266; B01F 11/0042; B01F 11/0045; B01F 11/0048; B01F 11/0051
USPC ................. 366/DIG. 3, DIG. 4, 108–128
See application file for complete search history.

(56) References Cited

U.S. PATENT DOCUMENTS

| | | | |
|---|---|---|---|
| 4,618,476 A * | 10/1986 | Columbus | 422/501 |
| 5,222,808 A | 6/1993 | Sugarman et al. | |
| 5,988,869 A | 11/1999 | Davidson et al. | |
| 6,916,113 B2 * | 7/2005 | Van de Goor et al. | 366/108 |
| 7,468,608 B2 * | 12/2008 | Feucht et al. | 324/633 |
| 8,038,337 B2 * | 10/2011 | Rathgeber et al. | 366/115 |
| 8,172,455 B2 * | 5/2012 | Noda | 366/173.1 |
| 8,517,596 B2 * | 8/2013 | Natarajan | 366/146 |
| 8,585,280 B2 * | 11/2013 | Natarajan | 366/275 |
| 2004/0037739 A1 | 2/2004 | McNeely et al. | |

(Continued)

FOREIGN PATENT DOCUMENTS

| | | |
|---|---|---|
| JP | 3135057 | 12/2000 |
| JP | 2002-521191 | 7/2002 |

(Continued)

*Primary Examiner* — Charles Cooley
(74) *Attorney, Agent, or Firm* — Fox Rothschild LLP

(57) ABSTRACT

A fluid agitation method is provided, whereby a swirling flow is generated in a trace amount of fluid, thereby agitating the fluid. The fluid agitation method includes introducing the fluid into an agitation chamber (3) including a wall having an uneven mass distribution, and applying oscillation (F) to the wall with frequencies varying in a predetermined frequency range. The uneven mass distribution of the wall is attained, for example, by arranging a plurality of thickened portions (11 to 18) of different thicknesses in a ring.

10 Claims, 15 Drawing Sheets

(56) References Cited

U.S. PATENT DOCUMENTS

| | | | |
|---|---|---|---|
| 2004/0228212 A1* | 11/2004 | de Goor et al. | 366/341 |
| 2006/0030796 A1 | 2/2006 | Xu et al. | |
| 2006/0125489 A1* | 6/2006 | Feucht et al. | 324/633 |
| 2006/0246490 A1 | 11/2006 | Anderson et al. | |
| 2006/0275883 A1* | 12/2006 | Rathgeber et al. | 435/173.1 |
| 2006/0285433 A1* | 12/2006 | Yang et al. | 366/341 |
| 2007/0002678 A1* | 1/2007 | Murakami | 366/116 |
| 2007/0007204 A1* | 1/2007 | Schanz et al. | 210/634 |
| 2007/0058483 A1* | 3/2007 | Aizenberg et al. | 366/127 |
| 2007/0237025 A1* | 10/2007 | Krupenkin et al. | 366/127 |
| 2008/0240992 A1 | 10/2008 | Murakami | |
| 2008/0247264 A1* | 10/2008 | Gabl et al. | 366/127 |
| 2011/0019497 A1* | 1/2011 | Kotera et al. | 366/116 |
| 2014/0192609 A1* | 7/2014 | Chi-Chan et al. | |

FOREIGN PATENT DOCUMENTS

| | | | |
|---|---|---|---|
| JP | 2005-169218 | 6/2005 | |
| JP | 2006-349380 | 12/2006 | |
| JP | 2007-101289 | 4/2007 | |
| JP | 2007-108062 | 4/2007 | |
| WO | WO 8300446 A1 * | 2/1983 | B01F 11/02 |

* cited by examiner

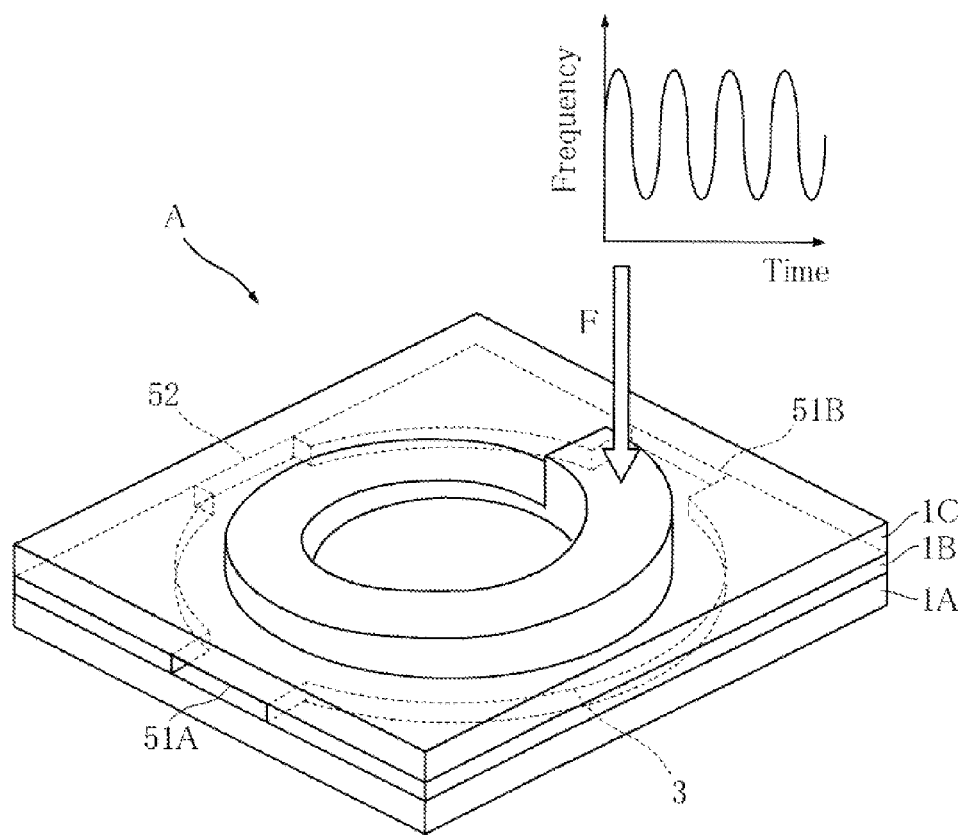

11Mode

21Mode

31Mode

12Mode

22Mode

41Mode (a)   (b)   (c)

(a)

(b)

(c)

Case1 : 8.9kHz(Fixed)

Case2 : 14, 20kHz(Step) 0.3sec

Case3 : 7.8-8.8kHz(Triangle) 5sec

Case4 : 4.3-6.8kHz(Triangle) 2sec

Case5 : 3.8-6.8kHz(Sine) 2sec

Case6 : 3.8-6.8kHz(Step) 0.3sec (a)   (b)

Case7 : 2.3-8.3kHz(Step) 0.3sec

1216Hz     1235Hz     1255Hz

1275Hz     1295Hz

Prior Art

FLUID AGITATION METHOD, FLUID AGITATION SYSTEM, AND CARTRIDGE

TECHNICAL FIELD

The present invention relates to a fluid agitation method and a fluid agitation system. The present invention also relates to a cartridge to be used in the fluid agitation system.

BACKGROUND ART

Health conditions can be checked by analyzing, for example, a specific component in the blood. Recently, analysis apparatuses of a relatively compact size have been developed for executing the component analysis. Some of the analysis apparatuses have a fluid agitation function of mixing the blood and a diluting fluid or mixing the diluted blood and a reagent, for performing the component analysis.

FIG. 18 depicts a cartridge X and an agitation arm 96 employed in a conventional fluid agitation method (see patent document 1 cited below). A main body 91 of the cartridge X includes a dilution chamber 92 for diluting blood 94 therein. The blood 94 introduced into the dilution chamber 92 is agitated with a diluting fluid 95. For performing the agitation, agitation particles 93 bearing magnetism are loaded in advance in the dilution chamber 92. The agitation arm 96 includes a pair of magnets spaced from each other, to be rotated about an axial center in a predetermined direction. When the agitation arm 96 rotates, the magnetic force of the respective magnets drives the agitation particle 93 to circulate, thereby mixing the blood 94 and the diluting fluid 95.
Patent document 1: Japanese Patent No. 3135057

Generally, only a trace amount of blood 94 (for instance, in the order of μL) is used for the component analysis. Accordingly, the agitation particle 93 must be minute in size. Also, the agitation particle 93 must not have such nature that disturbs the analysis of the specific component of the blood 94. However, employing the agitation particle 93 that satisfies such requirements leads to an increase in cost of the cartridge X. In the case, especially, where the cartridge X is of a disposable type, the increase in cost constitutes a major obstacle to regular practical use of the cartridge.

The conventional fluid agitation method has another drawback. As stated above, the circular movement of the agitation particle 93 is caused by magnetic force (non-contact force). Accordingly, the movement of the agitation particle 93 may fail to properly follow up the movement of the agitation arm 96, because of resistance of the blood 94 and so forth. This phenomenon becomes more prominent, in particular, with the increase in rotation speed of the agitation arm 96. Such failure leads to compromise in agitating force, thereby prolonging the time required for the specimen の analysis.

DISCLOSURE OF THE INVENTION

The present invention has been proposed under the foregoing situation. An object of the present invention is to provide a technique whereby fluid agitation can be performed more properly.

According to a first aspect of the present invention, there is provided a fluid agitation method that comprises: introducing a fluid into an agitation chamber including a wall whose mass distribution is uneven in a direction perpendicular to a thicknesswise direction of the wall; and applying oscillation to the wall with frequencies varying in a predetermined frequency range, thereby generating a swirling flow in the fluid.

The foregoing method eliminates the need to load an object for agitating the fluid in the agitation chamber, and also allows shifting a stagnation point of the swirling flow generated in the fluid. Such method allows promoting the agitation of the fluid.

Preferably, the frequency range includes a frequency at which the oscillation amplitude of the wall becomes maximum. Such arrangement causes the oscillation mode of the wall to prominently fluctuate at the frequency that makes the maximum oscillation amplitude of the wall. Therefore, the flow pattern of the swirling flow generated in the fluid can be prominently changed. This is advantageous for promoting the agitation of the fluid.

Preferably, the agitation chamber is circular, and the wall constitutes a bottom surface of the agitation chamber. Such structure is advantageous for generating the swirling flow in the fluid.

Preferably, the wall has a mass distribution uneven in a circumferential direction of the agitation chamber. Such structure allows efficiently changing the oscillation mode of the wall, which is circular.

Preferably, the wall is uneven in thickness so as to have an uneven mass distribution.

According to a second aspect of the present invention, there is provided a cartridge that comprises: an agitation chamber for agitating a fluid therein; and a micro channel communicating with the agitation chamber. The agitation chamber includes a wall whose mass distribution is uneven in a direction perpendicular to a thicknesswise direction of the wall.

Preferably, the agitation chamber is circular, and the wall constitutes a bottom surface of the agitation chamber.

Preferably, the wall has a mass distribution uneven in a circumferential direction of the agitation chamber.

Preferably, the wall is uneven in thickness so as to have an uneven mass distribution.

According to a third aspect of the present invention, there is provided a fluid agitation system that comprises: a cartridge according to the above-noted second aspect; and an excitation unit that applies oscillation to the wall with frequencies varying in a predetermined frequency range.

Preferably, the frequency range includes a frequency at which the oscillation amplitude of the wall becomes maximum.

BRIEF DESCRIPTION OF THE DRAWINGS

FIG. 3B is a perspective view showing a modification of the structure shown in FIG. 3A;

BEST MODE FOR CARRYING OUT THE INVENTION

Preferred embodiments of the present invention will be described below with reference to the accompanying drawings.

Figure 1:
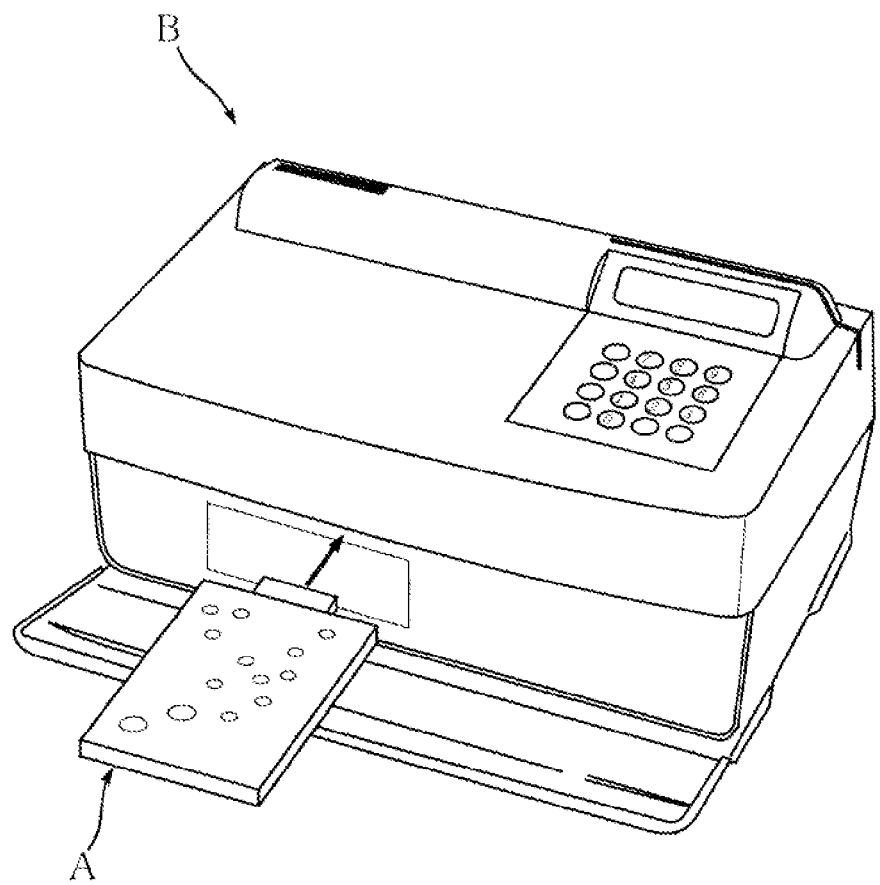
FIG. 1 is a perspective view showing an analysis apparatus that includes a fluid agitation system according to the present invention.

FIG. 1 depicts a specimen analysis system that employs a fluid agitation method according to the present invention. The specimen analysis system includes a cartridge A and a specimen analysis apparatus B. The cartridge A can be removably loaded in the specimen analysis apparatus B. To perform the specimen analysis, the cartridge A is spotted with the specimen, and loaded in the specimen analysis apparatus B. Then a predetermined agitation process (subsequently described) is performed with respect to the specimen in the cartridge A, which is followed by analysis of the specimen by the specimen analysis apparatus B. The specimen analysis apparatus B executes, for example by an optical technique, various measurement of specific components contained in the specimen. For example, in the case where the specimen is blood, measurement of blood cells (leukocyte, erythrocyte) contained in the blood and quantification of hemoglobin (Hb) or C-reactive protein (CRP) can be carried out. The specimen may be other than blood (for example, urine). Although the specimen is exemplified by blood in the following description, the present invention is in no way limited to such case.

The cartridge A includes, as will be described later in further details, a blood spotting portion, a diluting fluid chamber, an agitation chamber, an analysis unit, and a micro channel connecting those components. The cartridge A is of what is known as a disposable type, to be thrown away upon completion of an analysis job.

Figure 2:
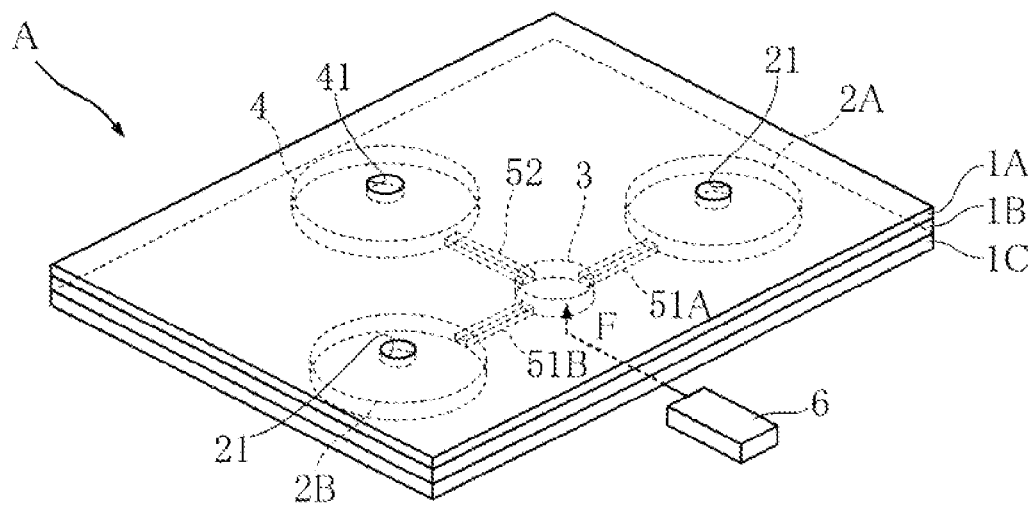
FIG. 2 is a perspective view showing an essential part of a cartridge employed in the fluid agitation system according to the present invention.

FIG. 2 depicts a portion of the cartridge A. A reference numeral 6 designates an actuator provided in the 0.20 specimen analysis apparatus B. The actuator 6 is located under the region in the specimen analysis apparatus B where the cartridge A is to be loaded. The actuator 6 is an example of the excitation unit, and includes for example a piezoelectric element and a cantilever extending therefrom. As shown in FIG. 2, the cartridge A is constituted of a top plate 1A, an intermediate plate 1B, and a bottom plate 1C adhered to each other. The top plate 1A, the intermediate plate 1B, and the bottom plate 1C are made of a silicone resin such as polydimethylsiloxane (PDMS). A plate member made of PDMS is highly flexible, and can easily oscillate once an excitation force is applied thereto. Here, as will be apparent from the following description, it is not mandatory to employ the silicone resin to form all of the top plate 1A, the intermediate plate 1B, and the bottom plate 1C. For example, only the bottom plate 1C may be made of the silicone resin, and the top plate 1A and the intermediate plate 1B may be made of a harder material such as an acrylic resin.

As shown in FIG. 2, the cartridge A includes a diluting fluid chamber 2A, a blood chamber 2B, an agitation chamber 3, a discharge chamber 4, and three channels 51A, 51B, and 52. The channel 51A communicates with the agitation chamber 3 and the diluting fluid chamber 2A; the channel 51B with the agitation chamber 3 and the blood chamber 2B; and the channel 52 with the agitation chamber 3 and the discharge chamber 4, respectively. Such structure can be built, for example, in the following process. First, four circular through holes (corresponding to the respective chambers 2A, 2B, 3, and 4) are formed, and three fine slits (or grooves) corresponding to the respective channels 51A, 51B, and 52, on a flat plate to be formed into the intermediate plate 1B. Then the top plate 1A is adhered to the upper surface of the intermediate plate 1B thus formed, and the bottom plate 1C to the lower surface of the intermediate plate 1B. Thus, the multilevel structure shown in FIG. 2 can be obtained. In the diluting fluid chamber 2A, a diluting fluid for diluting the blood is loaded. In the blood chamber 2B, the blood which is the specimen is stored. As already stated, the diluting fluid chamber 2A and the blood chamber 2B are connected to the agitation chamber 3 through the channels 51A, 51B, so that the prepared diluting fluid and blood are introduced into the agitation chamber 3 through these channels. In the agitation chamber 3, the diluting fluid and the blood are agitated and mixed, so that diluted blood is obtained. The diluted blood is delivered to the discharge chamber 4 from the agitation chamber 3, through the channel 52. As shown in FIG. 2, the top plate 1A includes two through holes 21 and a through hole 41 (these through holes are formed before adhering the top plate 1A to the intermediate plate 1B). The two through holes 21 communicate with the diluting fluid chamber 2A and the blood chamber 2B respectively, and the through hole 41 with the discharge chamber 4. The through holes 21, 41 are used to apply positive pressure or negative pressure necessary for feeding the blood, the diluting fluid, and the diluted blood.

Figure 3A:
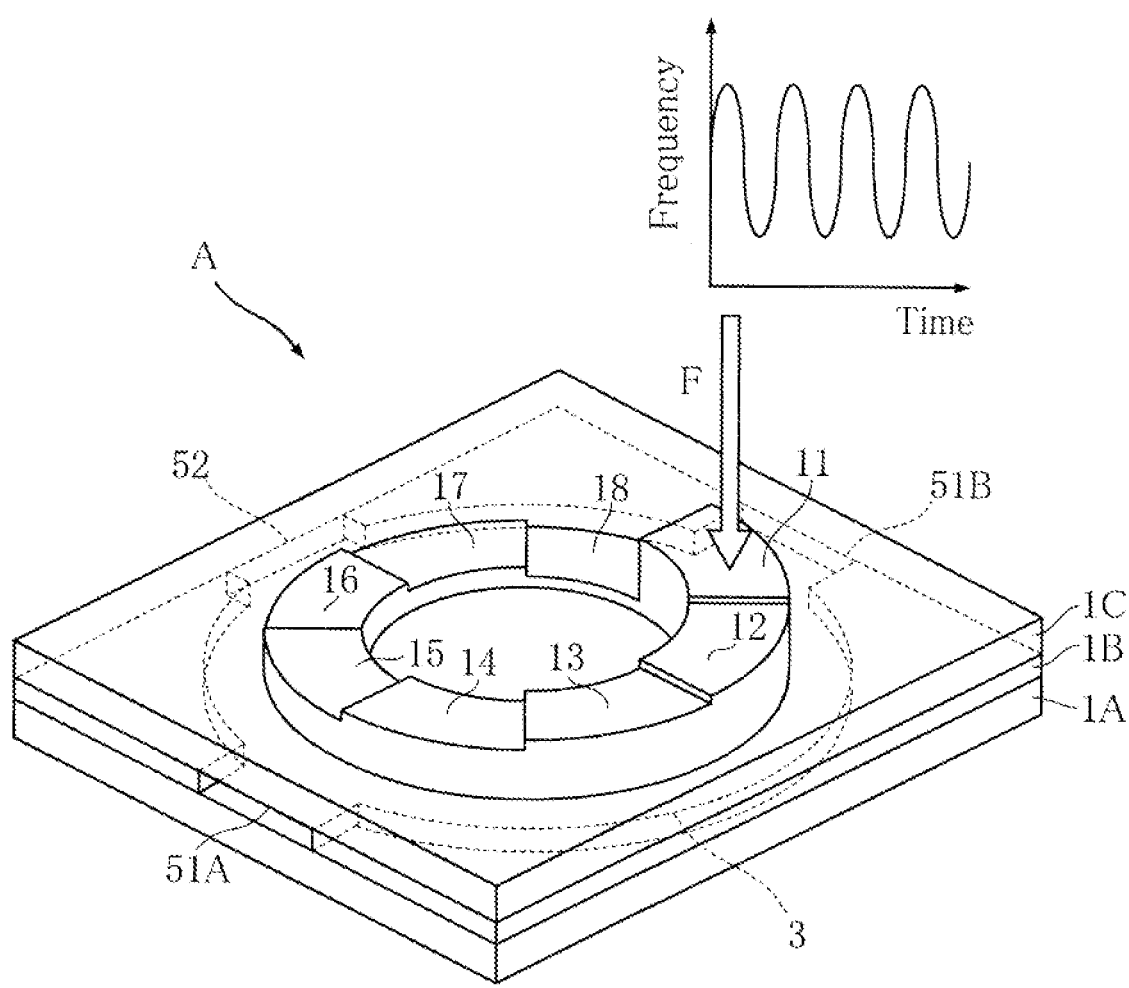
FIG. 3A is a perspective view showing an essential part of the cartridge.

FIG. 3A is a perspective view showing a portion of the cartridge A where the agitation chamber 3 is provided, while also showing relevant portions around the chamber (FIG. 3A shows portions upside down). As shown therein, on the surface of the bottom plate 1C (lower surface in FIG. 2), a plurality of thickened portions 11 to 18 is provided so as to extend in a ring shape. The thickened portions 11 to 18 each correspond to an area divided in eight (area having a central angle of 45° in an annular region (extending along the outer circumference of the agitation chamber 3) on the surface of the bottom plate 1C (accordingly, the thickened portions 11 to 18 have the same bottom area). The agitation chamber 3 is, for example, 1 mm in diameter and 50 μm in depth. The bottom plate 1C has a uniform thickness, which is for example 210 μm. The thickness of each of the thickened portions 11 to 18 (height with respect to the surface of the bottom plate 1C) is, for example, 80 μm, 70 μm, 60 μm, 50 μm, 40 μm, 30 μm, 20 μm, and 10 μm, respectively. The ring-shaped structure constituted of the thickened portions 11 to 18 has, for example, an outer diameter of 800 μm and an inner diameter of 500 μm. Since the thickness of the thickened portions 11 to decreases in steps as stated above, the mass of the thickened portions 11 to 18 also decreases in steps. Here, although it is assumed in the foregoing description that the thickened portions 11 to 18 and the bottom plate 1C are separately prepared members, and the thickness of the bottom plate 1C is uniform, different assumptions may be adopted. For example, it may be assumed that the thickened portions 11 to 18 are a part of the bottom plate 1C, and the bottom plate 1C has an uneven thickness at the positions corresponding to the ring-shaped thickened portions. In this case, for example the thickness of the bottom plate 1C at the region corresponding to the thickened portion 11 is 290 μm (210 μm+80 μm). FIG. 3B depicts a modified example of the structure shown in FIG. 3A. According to the present invention, the ring-shaped thickened portion may be formed such that the thickness steplessly varies, as shown in FIG. 3B. In this case, the upper surface of the ring-shaped thickened portion constitutes a smoothly inclined slope.

Figure 4:
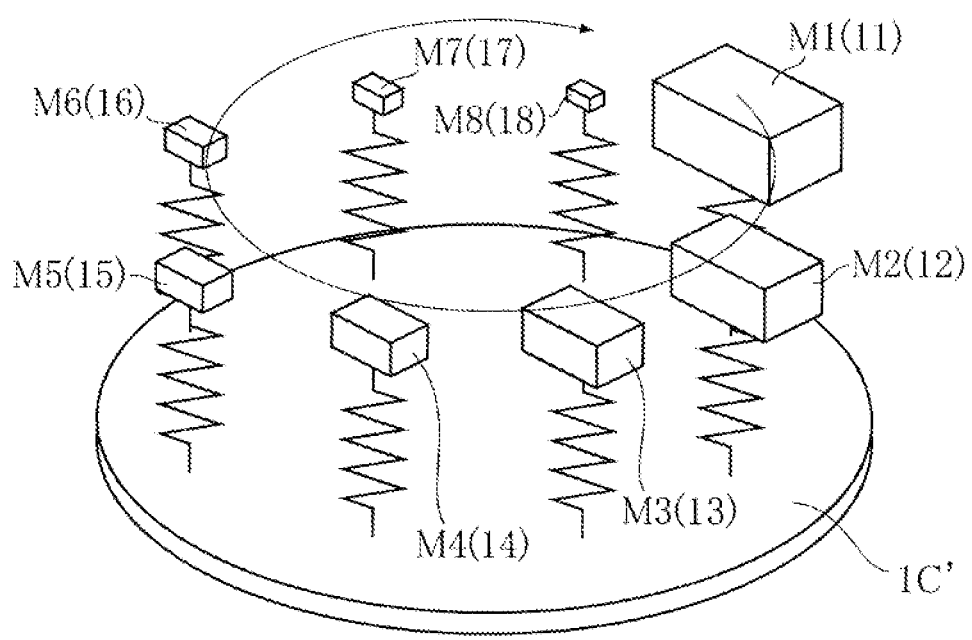
FIG. 4 is a schematic diagram for explaining the structure shown in FIG. 3A.

FIG. 4 shows a model for explaining the dynamic structure in the region shown in FIG. 3A. In this model, a plurality of weights (or mass points) M1 to M8 is disposed in a circle, and the weights are attached to the disk-shaped plate 1C' by means of a spring. The weights M1 to M8 respectively correspond to the thickened portions 11 to 18. Upon applying a vertically oscillating excitation force to the weight M1 (as indicated by an arrow F in FIG. 3A), the disk-shaped plate 1C' is caused to oscillate. As a result, one of the weights M1 to M8 prominently oscillates according to the frequency of the excitation force. When the frequency of the excitation force is changed, another weight prominently oscillates. Accordingly, the weights M1 to M8 can be sequentially made to prominently oscillate, by changing the frequency of the excitation force with the lapse of time.

Figure 5:
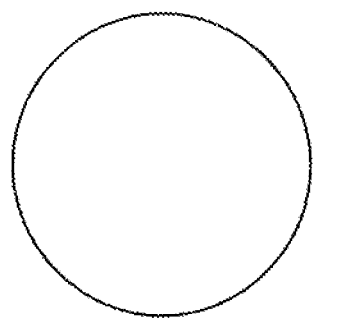
FIG. 5 includes diagrams showing a film oscillation mode of a bottom plate.
Figure 5:
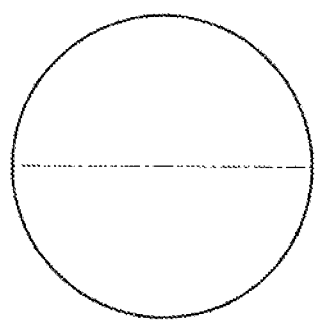
Figure 5:
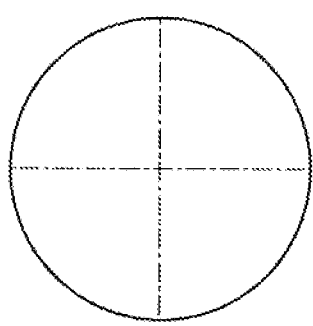
Figure 5:
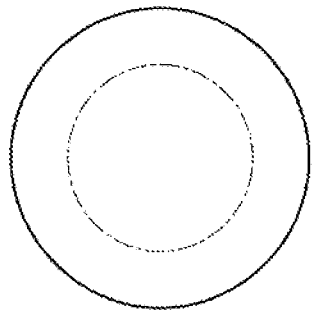
Figure 5:
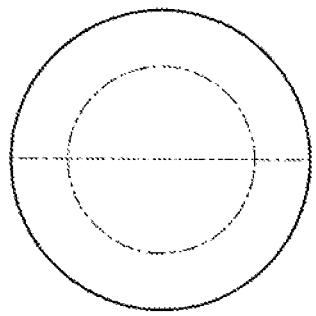
Figure 5:
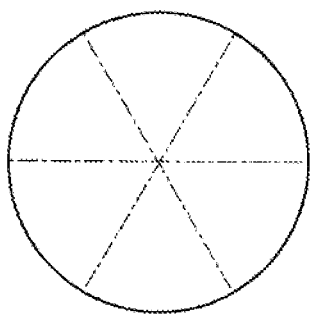

In the real structure (FIG. 3A), the circular portion of the bottom plate 1C (one of the walls constituting the agitation chamber 3) also oscillates, in addition to the oscillation of the thickened portions 11 to 18 (weights M1 to M8). FIG. 5 depicts the examples of the oscillation mode (in each mode, dash-dot lines represent a node of the oscillation). With the increase in frequency of oscillation applied to the circular portion of the bottom plate 1C, the respective oscillation modes appear as 11 mode, 21 mode, 31 mode, 12 mode, 22 mode, and 41 mode shown in FIG. 5.

Figure 6:
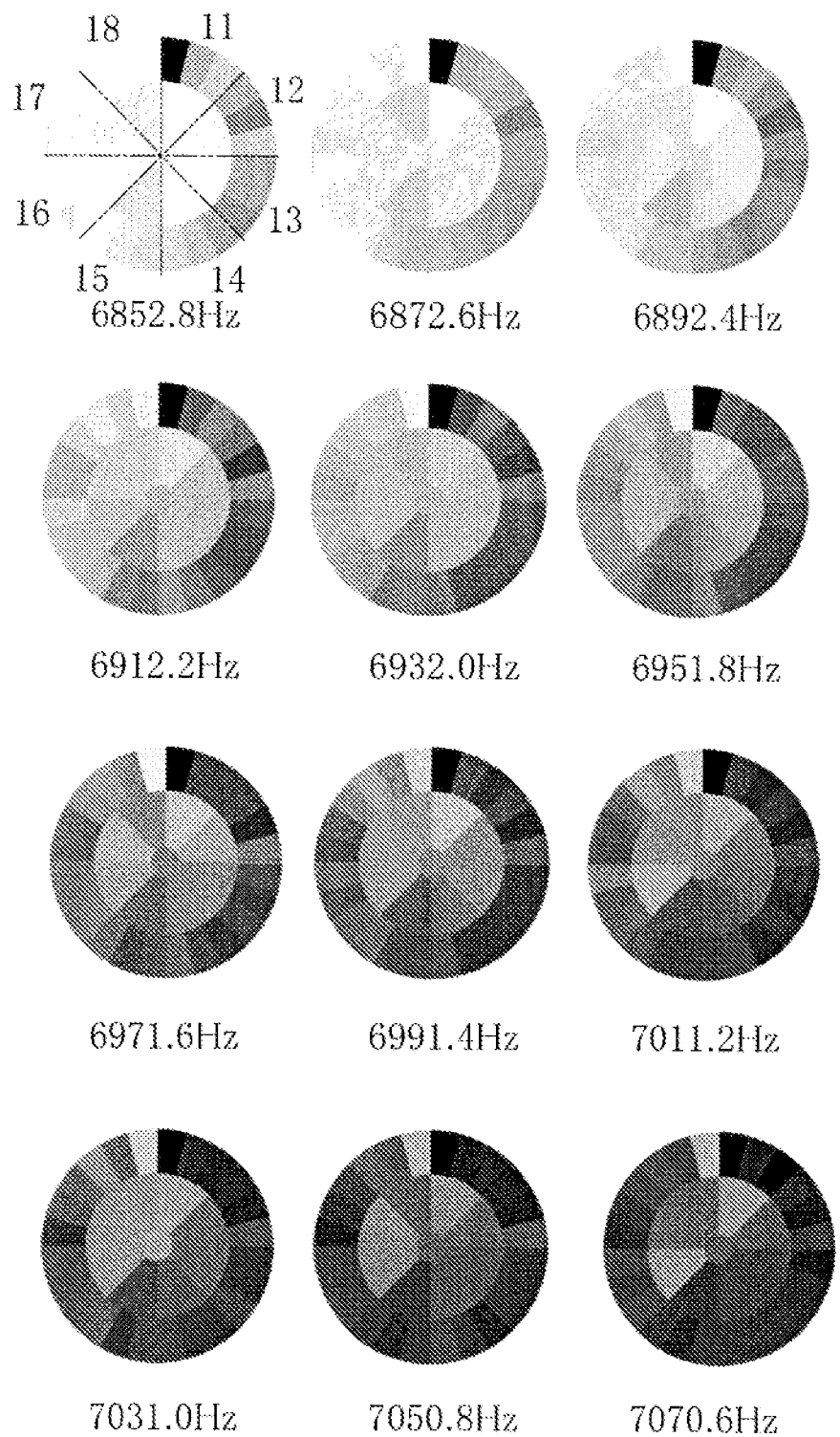
FIG. 6 includes diagrams showing an oscillation measurement result of the bottom plate.
Figure 7:
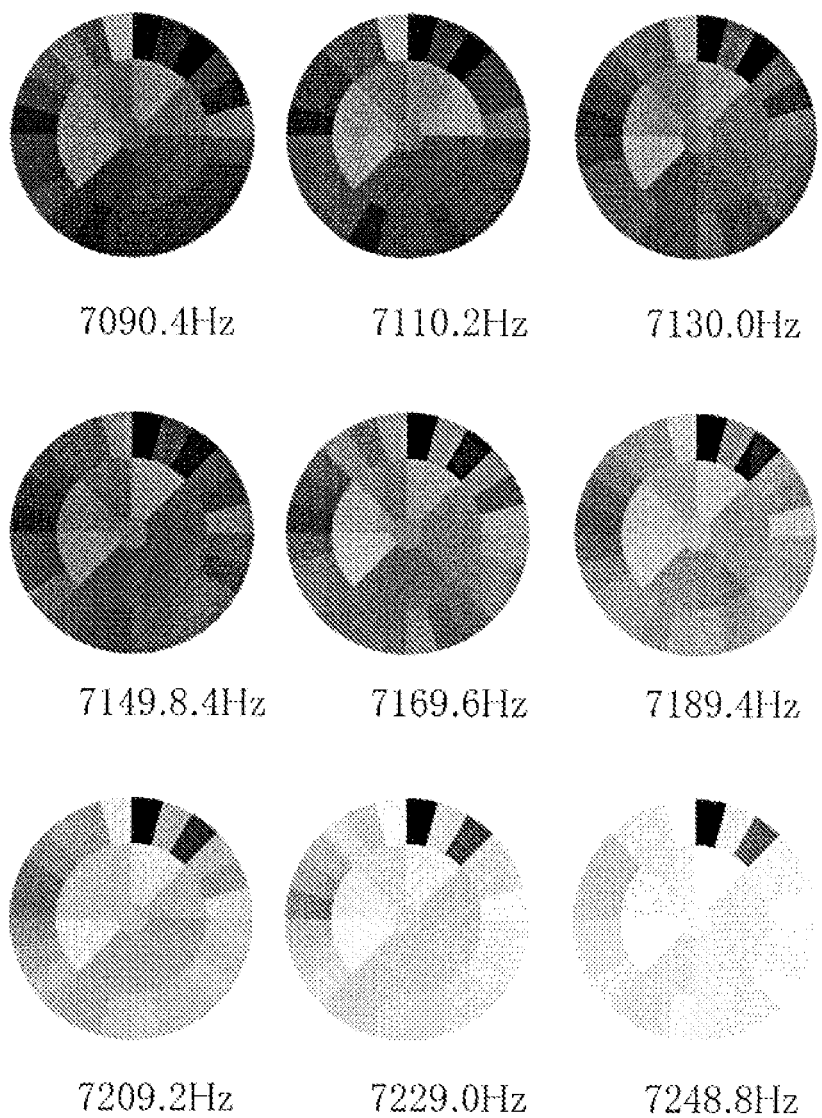
FIG. 7 includes diagrams showing an oscillation measurement result of the bottom plate.

Thus, the oscillation that takes place on the bottom plate 1C is a coupled oscillation composed of the oscillation of the weights M1 to M8 shown in FIG. 4 and the film oscillation shown in FIG. 5. The behavior of such coupled oscillation depends on the shape and size of the bottom plate 1C, and the shape, size, position and so forth of the thickened portions 11 to 18. FIGS. 6 and 7 illustrate results of simulation executed for investigating oscillation amplitude distribution produced when the bottom plate 1C oscillates. In this simulation, it is assumed that the excitation force F is applied to the thickened portion 11, as shown in FIG. 3A. In FIGS. 6 and 7, a portion of a relatively darker tone corresponds to a portion where the oscillation amplitude is relatively larger. Accordingly, a portion where the color tone is locally darker (portion of a relatively darker tone than the tone of adjacent portions) indicates the portion of the bottom plate 1C where the oscillation amplitude is maximum. Since it is assumed that the excitation force F is applied to the thickened portion 11 as stated above, the oscillation amplitude of the thickened portion 11 always remains relatively larger. As may be understood from FIGS. 6 and 7, an increase or decrease in frequency by approximately 20 Hz causes a prominent change in oscillation amplitude distribution and, in particular, shifts the portion on the bottom plate 1C where the oscillation amplitude becomes maximum. Here, although the fluctuation range of the frequency of the excitation force F is specified as 6852.8 Hz to 7248.8 Hz in this simulation, it is to be noted that such range is only exemplary and in no way limits the present invention. The frequency of the excitation force F may be set outside the foregoing range, for example at 4836.2 Hz, 4836.2 Hz, 4876 Hz, 0.4975.5 Hz, 4995 Hz, and 5134.7 Hz. In this simulation, the oscillation amplitude of (at least a part of) the bottom plate 1C becomes maximum, under such frequencies. Also, according to the present invention the number of thickened portions is not limited to eight, and the excitation force F may be applied to a portion other than the thickened portion 11.

Figure 8:
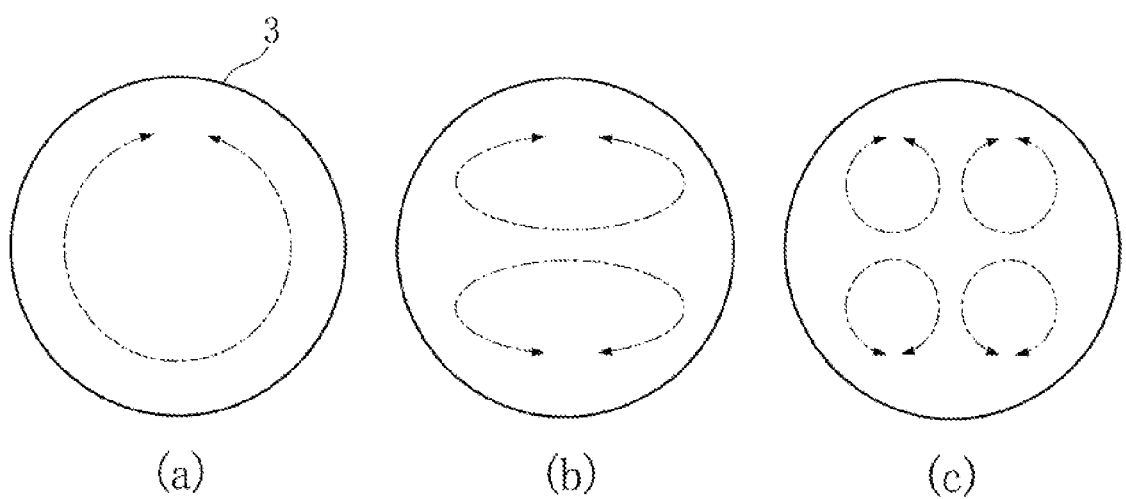
FIG. 8 shows flow patterns of a swirling flow.

The coupled oscillation of the bottom plate 1C generates a swirling flow in the blood and diluting fluid contained in the agitation chamber 3. FIG. 8 depicts typical flow patterns of the swirling flow. According to experiments performed by the present inventors, a coupled oscillation identical or similar to, for example, the 11 mode shown in FIG. 5 may generate the flow pattern shown in FIG. 8(a). As the mode of the coupled oscillation becomes more complicated, the flow patterns shown in FIG. 8(b) or 8(c) may appear. By changing the frequency of the excitation force F, these flow patterns may be sequentially generated in the agitation chamber 3, or normal and reverse rotation may repeatedly occur in the respective flow patterns.

After diluting the blood in the agitation chamber 3, the diluted blood is delivered to the discharge chamber 4. The specimen analysis apparatus B shown in FIG. 1 automatically executes counting of the blood cells or measurement of hemoglobin or C-reactive protein, with respect to the diluted blood.

The advantages of the foregoing fluid agitation method and the fluid agitation system will be described below.

Figure 18:
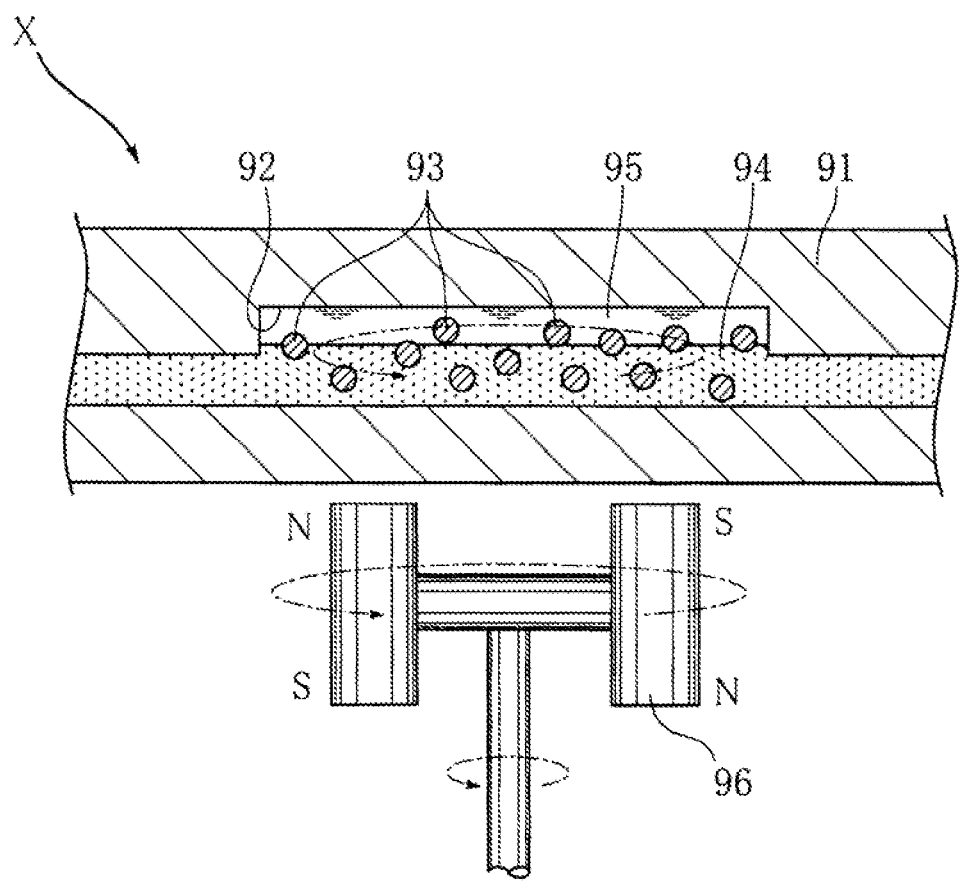
FIG. 18 illustrates a conventional fluid agitation method.

According to the present invention, the swirling flow of various patterns as shown in FIG. 8 can be generated, in the fluid in the agitation chamber 3. In those flow patterns, the position of the center (stagnation point) of the swirling flow is different from each other. Accordingly, utilizing these flow patterns in combination enables shifting the position of the stagnation point in the agitation chamber 3, and thereby preventing such failure that a portion of the fluid remains unagitated. According to the present invention, also, such desirable agitation can be performed without loading the agitation particles (numeral 93 in FIG. 18) or the like in the agitation chamber 3. This is advantageous for preventing contamination of the fluid to be agitated and reducing the cost of the cartridge A designed as the disposable type.

Further, the circular shape of the agitation chamber 3 allows easily generating therein the swirling flow. The annular alignment of the thickened portions 11 to 18 along the circular agitation chamber 3 enables largely changing the oscillation amplitude distribution in the bottom plate 1C as shown in FIG. 6, by changing the frequency. The prominent difference in oscillation amplitude distribution in the bottom plate 1C is advantageous for changing the flow pattern in the agitation chamber 3.

The thickened portions (weights) 11 to 18 are provided on the bottom plate 1C, on the opposite side of the agitation chamber 3. Such configuration facilitates locating the weights at a desired position with respect to the agitation chamber 3.

Figure 9:
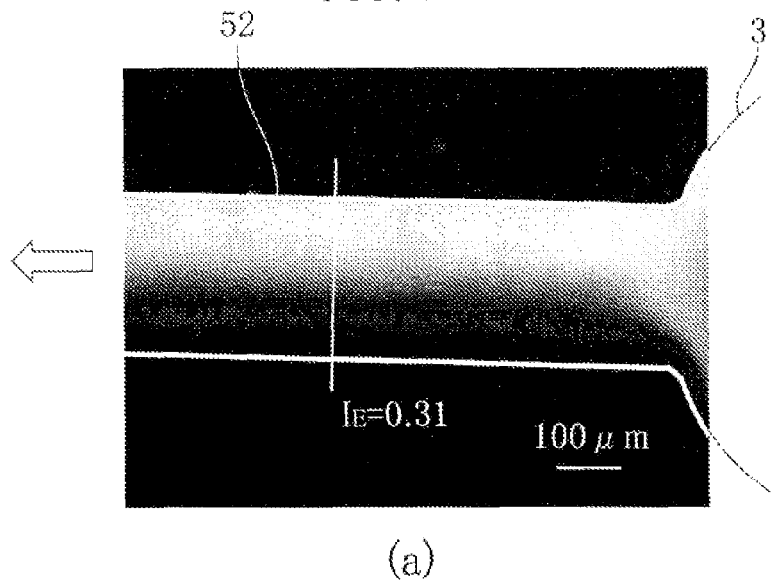
FIG. 9 shows the results of agitation tests conducted with an agitation chamber.
Figure 9:
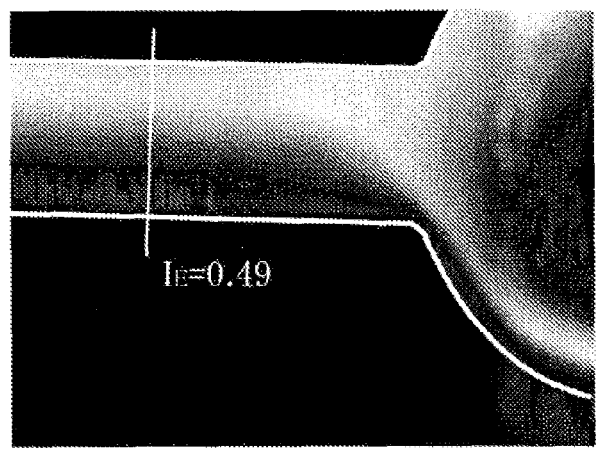
Figure 9:
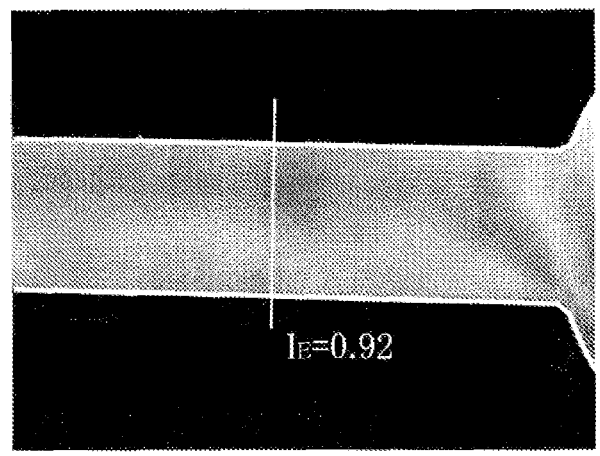

FIG. 9 shows the results of experiments for inspecting the agitation effect obtained by the fluid agitation method according to the present invention. In these experiments, two different fluids were introduced into the agitation chamber 3, and the degree of agitation attained at the moment of flowing out through the channel 52 was compared based on an agitation index $I_E$. The agitation index $I_E$ indicates zero when the two fluids are fully separated, and 1.0 when those fluids are agitated into a completely uniform mixture.

FIG. 9(a) shows the result of the experiment in which intentional agitation was not performed in the agitation chamber 3. In this case, the agitation index $I_E$ was 0.31. FIG. 9(b) shows the result of the experiment in which the excitation force F of a fixed frequency (f=8900 Hz) was applied to the bottom plate 1C. Despite that the frequency was fixed, generation of the swirling flow could be observed in the agitation chamber 3. In this case, the agitation index $I_E$ was 0.49, which proves that the swirling flow exhibited the agitation effect. FIG. 9(c) shows the result of the experiment in which the excitation force F of varying frequencies over a range of 4600 Hz to 9200 Hz was applied. This frequency range includes the foregoing frequencies of 4836.2 Hz, 4836.2 Hz, 4876 Hz, 4975.5 Hz, 4995 Hz, and 5134.7 Hz. In this case, it was confirmed that the swirling flow of different flow patterns was periodically generated in the agitation chamber 3. As a result, the agitation index $I_E$ was raised to as far as 0.92. It can be construed that generating the swirling flow of a plurality of flow patterns, in which the position of the stagnation point is shifted by turns, contributed to attaining such prominent agitation effect.

FIGS. 10 to 16 schematically depict the flow pattern in the agitation chamber 3, generated by the excitation force F of different frequencies. The condition of the excitation force F in the respective cases is shown in Table 1 given below. In these tests, the agitation chamber 3 was filled with a fluid containing minute tracer particles, and the movement caused by the excitation force F while the tracer particles were illuminated with light was pictured in video. FIGS. 10 to 16 show the flow pattern generated in the agitation chamber 3, drawn based on such video image.

TABLE 1

| Case No. | Frequency (kHz) | Pattern | Cycle |
|---|---|---|---|
| Case 1 | 8.9 | N/A | N/A |
| Case 2 | 14, 20 | Step | 2 sec |
| Case 3 | 7.8-8.8 | Triangle | 5 sec |
| Case 4 | 4.3-6.3 | Triangle | 2 sec |
| Case 5 | 3.8-6.8 | Sine | 2 sec |
| Case 6 | 3.8, 6.8 | Step | 0.3 sec |
| Case 7 | 2.3, 8.3 | Step | 0.3 sec |

Step: 
Triangle: 
Sine: 

Figure 10:
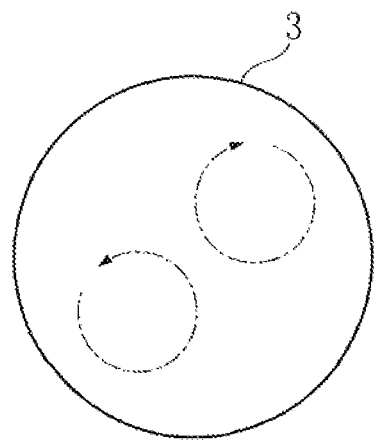
FIG. 10 is a diagram showing an agitation test result (case 1) in the agitation chamber.

In the case 1 shown in FIG. 10, the frequency of the excitation force F was fixed at 8.9 kHz. In this case, two swirls were formed in the agitation chamber 3. Such flow pattern did not change with the lapse of time. This state is similar to the state shown in FIG. 9(b). Although the fluid in the agitation chamber 3 was agitated, stagnation points emerged because the flow pattern remained unchanged. It can be presumed that it was for such reason that the agitation index $I_E$ could not be better than 0.49 in the case of FIG. 9(b).

Figure 11:
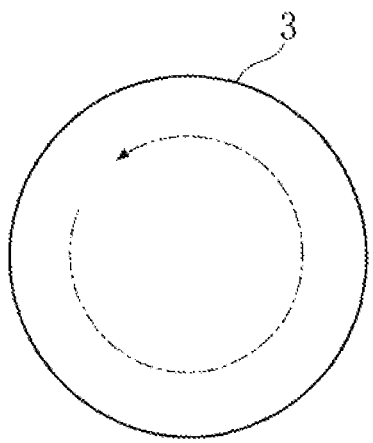
FIG. 11 is a diagram showing an agitation test result (case 2) in the agitation chamber.
Figure 12:
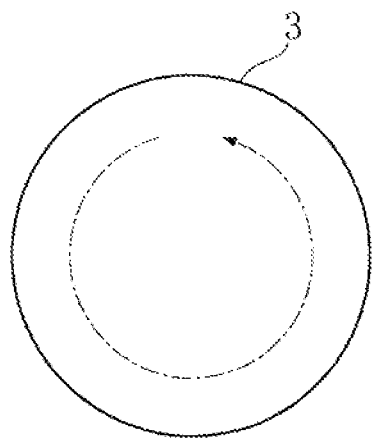
FIG. 12 is a diagram showing an agitation test result (case 3) in the agitation chamber.
Figure 13:
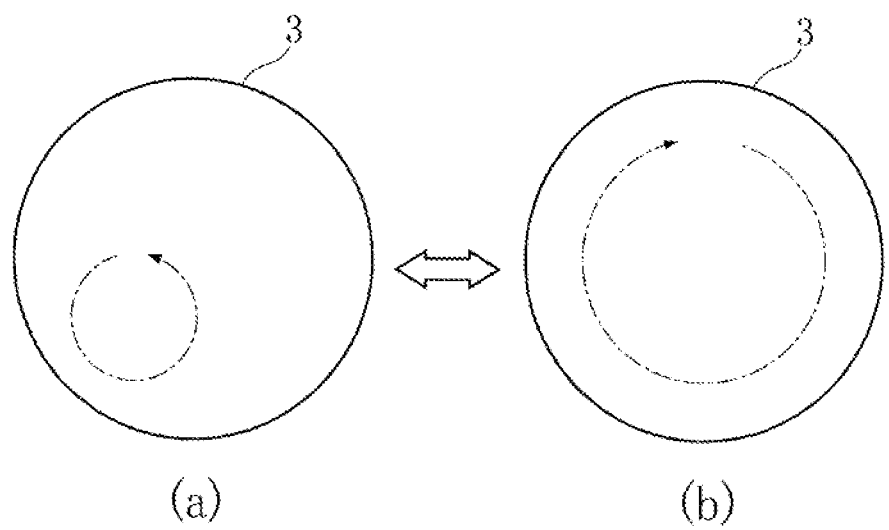
FIG. 13 shows the results of agitation tests (case 4) with the agitation chamber.
Figure 14:
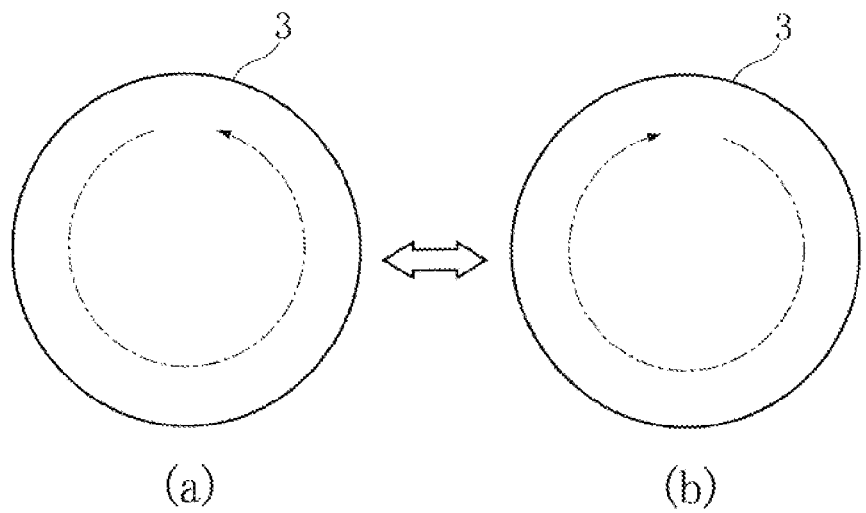
FIG. 14 shows the results of agitation tests (case 5) with the agitation chamber.
Figure 15:
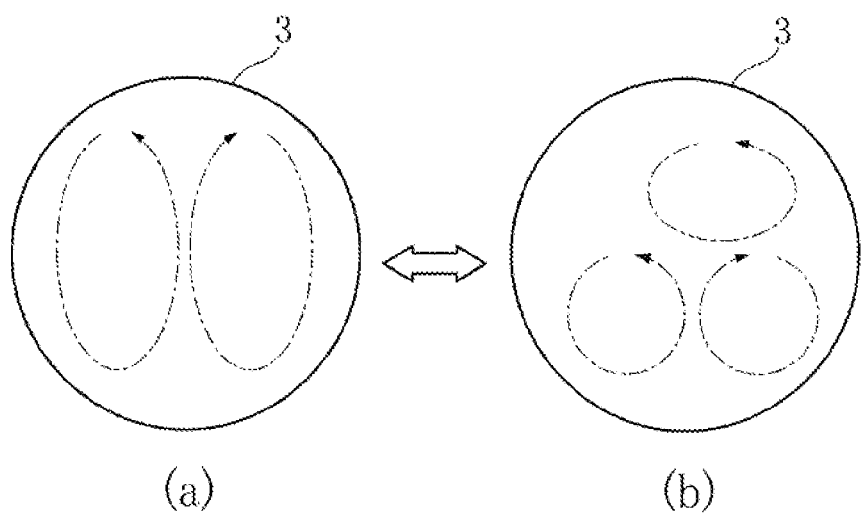
FIG. 15 shows the results of agitation tests (case 6) with the agitation chamber.
Figure 16:
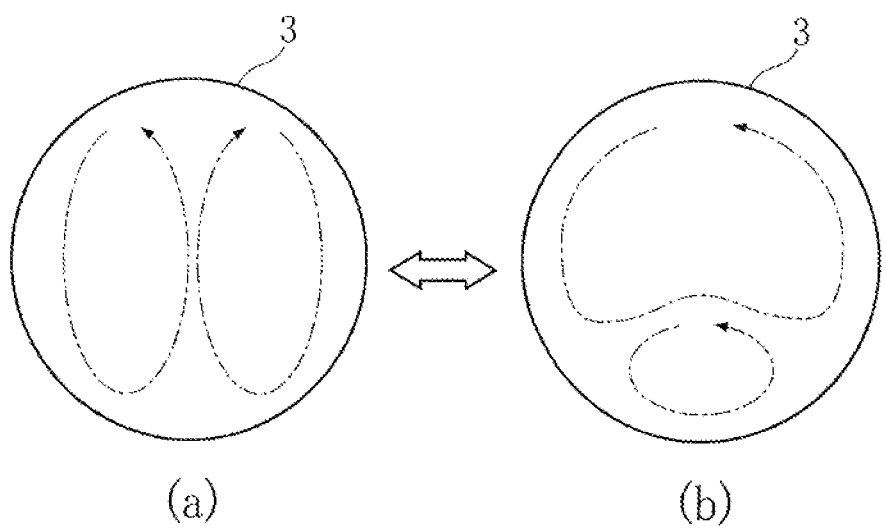
FIG. 16 shows the results of agitation tests (case 7) with the agitation chamber.

In the case 2 shown in FIG. 11, the frequency of the excitation force F was changed in steps between 14 kHz and 20 kHz (in other words, the frequency was alternately set at 14 kHz and 20 kHz). In this case, a large swirl was formed in the agitation chamber 3. Because of the relatively high frequency, the rotation speed of the swirl was comparatively high. In the case 3 shown in FIG. 12, the frequency was changed in a triangle wave shape (linearly increased and decreased) between 7.8 kHz and 8.8 kHz with the lapse of time. In this case also, the flow pattern remained generally unchanged.

In the cases 4 to 7 respectively shown in FIGS. 13 to 16, at least two flow patterns repeatedly appeared in the agitation chamber 3. With such flow patterns, the stagnation points did not stay at one position in the agitation chamber 3, and hence the entirety of the agitation chamber 3 could be uniformly agitated. These cases are similar to the state shown in FIG. 9(c). It can be construed that the factor that raised the agitation index $I_E$ up to as high as 0.92 in the case of FIG. 9(c) was such fluctuation of the flow patterns.

Figure 17:
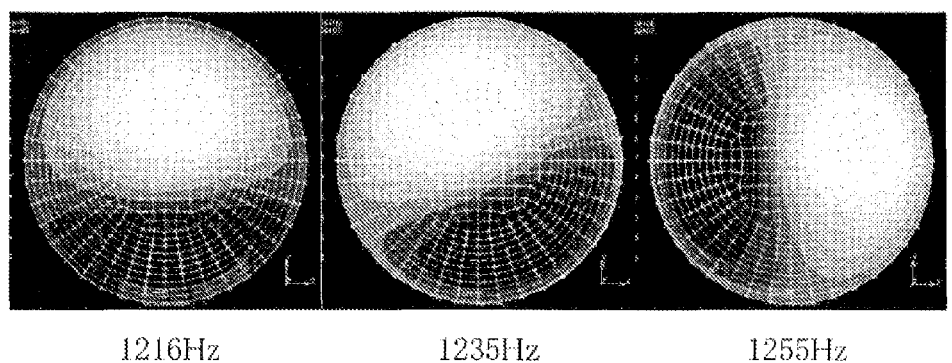
FIG. 17 shows diagrams for illustrating the results of an oscillation amplitude distribution analysis with the use of a speaker for excitation.
Figure 17:
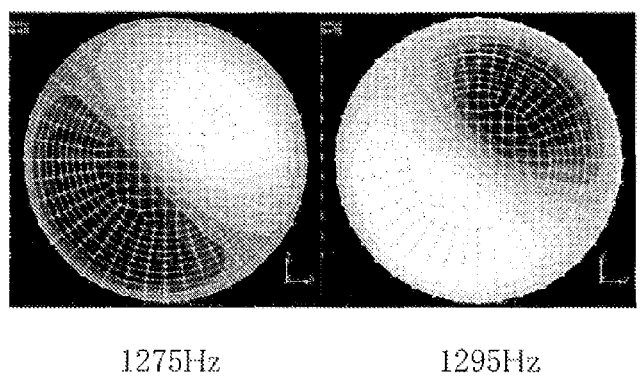

According to the present invention, the structure of the excitation unit is not limited to the contact-type that employs the piezoelectric element and the cantilever. For example, a non-contact configuration that utilizes a speaker (oscillation film) may be adopted. FIG. 17 shows analysis results of oscillation response obtained upon applying the excitation force F with the speaker to a wall having the uneven mass distribution similar to that of the bottom plate 1C. The wall had a thickness of 140 μm, and the thickness of the thickened portion was set in a range of 50 to 400 μm. The frequency of the excitation force F was changed from 1216 Hz to 1295 Hz. In FIG. 17, a whiter region represents a portion with larger oscillation amplitude. Such non-contact type excitation unit can still change the oscillation amplitude distribution of the wall by changing the frequency, thereby generating the swirling flow of different flow patterns in the fluid.

It is to be understood that the present invention is not limited to the foregoing embodiment. For example, the disposition of the thickened portions 11 to 18 is not limited to the ring shape, but may be otherwise arranged provided that the oscillation mode can prominently change according to the fluctuation in frequency of the excitation force F. To make the mass distribution of the bottom plate 1C uneven, integrally forming the thickened portions 11 to 18 with the bottom plate 1C is not the only option. For example, a plurality of metal members may be discretely attached to the bottom plate 1C. Alternatively, a paint having relatively high density may be discretely and unevenly printed on the bottom plate 1C. Further, the density distribution of the bottom plate 1C having a uniform thickness may be set locally uneven. The shape of the agitation chamber 3 is not limited to a circle, but may be different provided that the shape is appropriate for generating the swirling flow in the fluid introduced into the agitation chamber. The wall to which the uneven mass distribution is given is not limited to the bottom plate 1C, but may be another wall constituting the agitation chamber 3.

The invention claimed is:

1. A method of agitating a fluid, comprising:
   introducing a fluid into an agitation chamber including a wall whose mass distribution is uneven in a direction perpendicular to a thicknesswise direction of the wall; and
   applying a vertically oscillating excitation force to the wall with frequencies varying in a predetermined frequency range, thereby generating a swirling flow in the fluid.

2. The method according to claim 1, wherein the frequency range includes a frequency at which oscillation amplitude of the wall becomes maximum.

3. The method according to claim 1, wherein the agitation chamber is circular, and the wall constitutes a bottom surface of the agitation chamber.

4. The method according to claim 3, wherein the wall has a mass distribution uneven in a circumferential direction of the agitation chamber.

5. The method according to claim 1, wherein the wall is uneven in thickness so as to have an uneven mass distribution.

6. A fluid agitation system comprising a cartridge and an excitation unit, the cartridge comprising:
   an agitation chamber for agitating a fluid therein; and
   a micro channel communicating with the agitation chamber;
   wherein the agitation chamber includes a wall whose mass distribution is uneven in a direction perpendicular to a thicknesswise direction of the wall; and wherein the excitation Unit a lies a vertically oscillating excitation force to the wall with frequencies varying in a predetermined frequency range.

7. The fluid agitation system according to claim 6, wherein the agitation chamber is circular, and the wall constitutes a bottom surface of the agitation chamber.

8. The fluid agitation system according to claim 7, wherein the wall has a mass distribution uneven in a circumferential direction of the agitation chamber.

9. The fluid agitation system according to claim 6, wherein the wall is uneven in thickness so as to have an uneven mass distribution.

10. The fluid agitation system according to claim 6, wherein a frequency range of the oscillation includes a frequency at which an amplitude of the wall becomes maximum.

* * * * *